(12) United States Patent
Kagechika et al.

(10) Patent No.: US 7,314,639 B2
(45) Date of Patent: Jan. 1, 2008

(54) PROCESS FOR THE PRODUCTION OF CRYSTALS OF A BENZOIC ACID DERIVATIVE

(75) Inventors: Hiroyuki Kagechika, Tokyo (JP); Hiroo Nagano, Osaka (JP)

(73) Assignees: Toko Pharmaceutical Ind. Co., Ltd., Tokyo (JP); Research Foundation Itsuu Laboratory, Tokyo (JP)

( * ) Notice: Subject to any disclaimer, the term of this patent is extended or adjusted under 35 U.S.C. 154(b) by 0 days.

(21) Appl. No.: 10/344,690

(22) PCT Filed: Aug. 31, 2001

(86) PCT No.: PCT/JP01/07526

§ 371 (c)(1), (2), (4) Date: Feb. 24, 2003

(87) PCT Pub. No.: WO02/18322

PCT Pub. Date: Mar. 7, 2002

(65) Prior Publication Data

US 2003/0191342 A1    Oct. 9, 2003

(30) Foreign Application Priority Data

Sep. 1, 2000  (JP) .............................. 2000-264733

(51) Int. Cl.
*A61K 9/14*    (2006.01)
(52) U.S. Cl. .............. 424/489; 252/301.16; 252/299.01
(58) Field of Classification Search ................ 424/489; 252/301.16, 299.01
See application file for complete search history.

(56) References Cited

U.S. PATENT DOCUMENTS 4,104,297 A  *  8/1978  Buxbaum et al. ........... 528/289
4,703,110 A     10/1987  Shudo
5,214,202 A  *  5/1993  Hamada et al. ............. 562/457

FOREIGN PATENT DOCUMENTS

| EP | 0170105 | 2/1986 |
| EP | 0478787 | 4/1992 |
| JP | 61-22047 | 1/1986 |
| JP | 61-76440 | 4/1986 |
| JP | 3001632 | 11/1999 |
| JP | 2000-34262 | 2/2000 |
| WO | 91/14673 | 10/1981 |

OTHER PUBLICATIONS

English Language Abstract of WO91/14673.
English Language Abstract of JP 2000-34262.
English Language Abstract of JP 61-76440.
Chem. Pharm. Bull., 32, p. 4209-4212, (1984).
J. Cellular Physiology, 135, 179-188 (1988).
English Language Abstract of JP 61-22047.
Kagechika, H. et al., J. Med. Chem. 31, vol. 31 (No. 11), 2182-2192 (1988).
Toriumi, Y. et al., J. Org. Chem., vol. 55 (No. 1), 259-263(1990).

* cited by examiner

*Primary Examiner*—Dameron L. Jones
(74) *Attorney, Agent, or Firm*—Greenblum & Bernstein, P.L.C.

(57) ABSTRACT

A method for preparing a crystal of 4-[(5,6,7,8-tetrahydro-5,5,8,8-tetramethyl-2-naphthalenyl)carbamoyl]benzoic acid having a single endothermic peak approximately at 233° C. in differential scanning calorimetry, which comprises the step of recrystallizing a crystal of 4-[(5,6,7,8-tetrahydro-5,5,8,8-tetramethyl-2-naphthalenyl)carbamoyl]benzoic acid from a mixture of water and ethanol. The method enables selective preparation of type-II crystals which are stable against physical impact. The resulting crystals are free from highly toxic hexane as a residual solvent, and preferably used as an active ingredient of pharmaceuticals.

15 Claims, No Drawings

US 7,314,639 B2

PROCESS FOR THE PRODUCTION OF CRYSTALS OF A BENZOIC ACID DERIVATIVE

TECHNICAL FIELD

The present invention relates to a method for selective preparation of a particular crystal of 4-[(5,6,7,8-tetrahydro-5,5,8,8-tetramethyl-2-naphthalenyl)carbamoyl]benzoic acid useful as an active ingredient of a medicament.

BACKGROUND ART

4-[(5,6,7,8-Tetrahydro-5,5,8,8-tetramethyl-2-naphthalenyl)carbamoyl]benzoic acid has retinoid activity, and its use as an active ingredient of a medicament has been expected. Conventionally, this compound is known to exist at least as two kinds of crystal polymorphs, that is, (1) a crystal melting at 193° C. and (2) a crystal melting at 233° C. [see, Japanese Patent No. 3001632 as for (1), and Japanese Patent Unexamined Publication (Kokai) No. 61-76440 as for (2). (3) A crystal melting at 205.5° C. to 206.5° C. is disclosed in Chem. Pharm. Bull., 32, p.4209, 1984. However, this crystal was later reported to actually have the melting point of 231° C. to 232° C. and thus revealed to be identical to the crystal (2) (J. Cellular Physiology, 135, pp.179-188, 1988)].

The crystal described in Japanese Patent No. 3001632, which melts at 193° C., is prepared by using a mixture of methanol and water as a recrystallization solvent. The crystal that melts at 233° C. is prepared by using a mixture of ethyl acetate and hexane as a recrystallization solvent. The latter crystal (melting point: 233° C.) contains 1200 ppm and 190 ppm of residual ethyl acetate and hexane, respectively, and thus has a problem that the crystal can hardly satisfy the standard values of residual solvents provided by the Ministry of Health and Welfare (ethyl acetate: 5000 ppm or less; hexane: 290 ppm). Whilst, the crystal that melts at 193° C. has a characteristic feature that a residual methanol level can be significantly lowered.

However, the crystal that melts at 193° C. has a problem that the crystalline form readily occurs transition by physical impact, and thus preparation thereof as a uniform crystal is extremely difficult. Accordingly, this crystal lacks an aptitude as a raw material for large scale manufacture of a pharmaceutical product that constantly meets quality standard. Whilst the crystal that melts at 233° C. has been revealed to have high stability against physical impact, as well as against heat, temperature, light and the like. However, a method for selective preparation of this crystal has not been known so far. Further, a method is known for preparation of the crystal that melts at 233° C. in which a mixture of ethyl acetate and hexane are used as a recrystallization solvent. However, hexane is classified as Class 2 solvent according to the guidelines for residual solvents of pharmaceutical products, and is undesirable solvent to be remained in pharmaceutical preparations. Accordingly, a crystal is strongly desired that does not contain hexane as a residual solvent.

DISCLOSURE OF THE INVENTION

An object of the present invention is to provide a method for selective preparation of the crystal that melts at 233° C. among crystals of 4-[(5,6,7,8-tetrahydro-5,5,8,8-tetramethyl-2-naphthalenyl)carbamoyl]benzoic acid, and the above crystal that does not contain hexane as residual solvent.

The inventors of the present invention conducted various studies to achieve the foregoing object. As a result, they found that the crystal that melts at 233° C. can be selectively prepared by recrystallization using a mixture of ethanol and water. Conventionally, it has been known that the crystal that melts at 193° C. can be selectively prepared by using a mixture of ethanol and water. It is indeed surprising that the crystal of different crystalline form can be selectively obtained by using the mixture of ethanol and water.

The present invention thus provides a method for preparing a crystal of 4-[(5,6,7,8-tetrahydro-5,5,8,8-tetramethyl-2-naphthalenyl)carbamoyl]benzoic acid having a single endothermic peak approximately at 233° C. in differential scanning calorimetry, which comprises the step of recrystallizing a crystal of 4-[(5,6,7,8-tetrahydro-5,5,8,8-tetramethyl-2-naphthalenyl)carbamoyl]benzoic acid from a mixture of water and ethanol. According to a preferred embodiment, the aforementioned method wherein a volume ratio of ethanol and water is in the range of 8:5 to 1:1 is provided.

The present invention also provides a method for preparing a crystal of 4-[(5,6,7,8-tetrahydro-5,5,8,8-tetramethyl-2-naphthalenyl)carbamoyl]benzoic acid having a single endothermic peak approximately at 233° C. in differential scanning calorimetry, which comprises the step of heating a crystal of 4-[(5,6,7,8-tetrahydro-5,5,8,8-tetramethyl-2-naphthalenyl)carbamoyl]benzoic acid having endothermic peaks approximately at 193° C. and 233° C. in differential scanning calorimetry. According to a preferred embodiment, the crystal can be heated at a temperature around 200° C.

From another aspect of the present invention, there is also provided a crystal of 4-[(5,6,7,8-tetrahydro-5,5,8,8-tetramethyl-2-naphthalenyl)carbamoyl]benzoic acid having a single endothermic peak approximately at 233° C. in differential scanning calorimetry, which is characterized not to contain hexane and/or ethyl acetate as a residual solvent. The present invention further provides a crystal of 4-[(5,6,7,8-tetrahydro-5,5,8,8-tetramethyl-2-naphthalenyl)carbamoyl]benzoic acid having a single endothermic peak approximately at 233° C. in differential scanning calorimetry, which contains 2,000 ppm or less of residual ethanol after the crystal is dried at 110° C. to 120° C. under reduced pressure, and a crystal of 4-[(5,6,7,8-tetrahydro-5,5,8,8-tetramethyl-2-naphthalenyl)carbamoyl]benzoic acid having endothermic peaks approximately at 193° C. and 233° C. in differential scanning calorimetry.

Further, the present invention provides use of a crystal of the 4-[(5,6,7,8-tetrahydro-5,5,8,8-tetramethyl-2-naphthalenyl)carbamoyl]benzoic acid having a single endothermic peak approximately at 233° C. in differential scanning calorimetry, which is characterized not to contain hexane and/or ethyl acetate as a residual solvent, for manufacture of a pharmaceutical product, and a medicament comprising the aforementioned crystal as an active ingredient. Examples of the aforementioned medicament include a medicament for therapeutic treatment of acute promyelocytic leukemia, a medicament for therapeutic treatment of psoriasis and pustulosis palmaris et plantaris and the like.

BEST MODE FOR CARRYING OUT THE INVENTION

Types of crystals of 4-[(5,6,7,8-tetrahydro-5,5,8,8-tetramethyl-2-naphthalenyl)carbamoyl]benzoic acid used as a raw material for the method of the present invention are not particularly limited. Any crystals may be used in addition to the crystal that melts at 193° C. (the aforementioned crystal (1)). According to the studies of the inventors of the present invention, the crystal that melts at 193° C. (referred to as "type-I crystal") described in Japanese Patent No. 3001632 gives a single endothermic peak approximately at 194° C. in differential scanning calorimetry (DSC). Further, the crystal that melts at 233° C. (referred to as "type-I crystal")

described in Japanese Patent Unexamined Publication No. 61-76440 gives a single endothermic peak approximately at 233° C. in differential scanning calorimetry. Besides these crystals, the inventors of the present invention has recognized the existence of a crystal that gives an endothermic peak approximately at 193° C. in differential scanning calorimetry and simultaneously occurs exothermic transition to give an endothermic peak approximately at 233° C. (referred to as "type-III crystal", see, Example 3 of the specification). In the specification, this crystal is defined as a crystal of 4-[(5,6,7,8-tetrahydro-5,5,8,8-tetramethyl-2-aphthalenyl)carbamoyl]benzoic acid that has endothermic peaks approximately at 193° C. and 233° C. in differential scanning calorimetry. Any of the aforementioned crystals may be used as a raw material for the method of the present invention.

Crystalline forms can be reliably identified by performing powder X-ray diffraction analysis in addition to differential scanning calorimetry. Powder X-ray diffraction patterns of the aforementioned type-I and type-II crystals are shown in FIGS. 5 and 6 of Japanese Patent No. 3001632 and can be easily identified by those skilled in the art. Further, the results of thermal analyses of the aforementioned type-I and type-II crystals are shown in FIGS. 3 and 4 of the aforementioned patent document, respectively. An experimental error in measurement of melting point, differential scanning calorimetry and the like is approximately a few degrees, usually within 2° C., preferably within 1° C., more preferably within 0.5° C.

The method of the present invention is characterized in that a mixture of ethanol and water is used as a recrystallization solvent for 4-[(5,6,7,8-tetrahydro-5,5,8,8-tetramethyl-2-naphthalenyl)carbamoyl]benzoic acid. A mixing ratio of ethanol and water at crystallization is not particularly limited. For example, ethanol:water is preferably in the range of about 8:5 to 1:1. When the proportion of ethanol become higher than the above range, a mixture of type-I crystals and type-II crystals may sometimes be obtained.

A process for recrystallization is not particularly limited, and an ordinary recrystallization process may be employed. For example, a crystal of 4-[(5,6,7,8-tetrahydro-5,5,8,8-tetramethyl-2-naphthalenyl)carbamoyl]benzoic acid as a raw material may be completely dissolved in a mixture of ethanol and water, and then the solution may be gradually cooled and precipitated crystals are collected by filtration. Alternatively, a crystal as a raw material may be dissolved in ethanol with heating, and then the solution may be added with an appropriate amount of hot water to prepare an ethanol-water mixture in a given ratio for crystallization of the desired substance. In order to efficiently crystallize the objective substance, a seed crystal may be added. An amount of the seed crystal is not particularly limited. The amount may be about 1/1,000 to 1/1,000,000, preferably about 1/80,000, based on the weight of the crystal used as a raw material. The crystals collected by filtration can be generally dried with heating at about 110° C. to 120° C. under reduced pressure to remove the recrystallization solvent.

Further, when a crystal of 4-[(5,6,7,8-tetrahydro-5,5,8,8-tetramethyl-2-naphthalenyl)carbamoyl]benzoic acid having endothermic peaks approximately at 193° C. and 233° C. in differential scanning calorimetry is heated to obtain a crystal of 4-[(5,6,7,8-tetrahydro-5,5,8,8-tetramethyl-2-naphthalenyl)carbamoyl]benzoic acid having a single endothermic peak approximately at 233° C. in differential scanning calorimetry, a heating temperature may generally be 180° C. or higher, preferably 200° C. or higher, most preferably about 200° C. to 210° C.

The crystal of 4-[(5,6,7,8-tetrahydro-5,5,8,8-tetramethyl-2-naphthalenyl)carbamoyl]benzoic acid provided by the method of the present invention is manufactured without using a recrystallization solvent containing hexane, and accordingly, the crystal is characterized not to substantially contain hexane as a residual solvent. For example, after dryness with heating at 110° C. to 120° C. under reduced pressure of 30 mmHg or lower for 22 hours, residual ethanol contained in the crystals is usually 2,000 ppm or less, preferably 1,000 ppm or less, more preferably 500 ppm or less. Ethanol is a low toxic solvent which is classified as Class 3 solvent among residual solvents in pharmaceutical products according to provisions by the Ministry of Health and Welfare. Accordingly, the crystal of the present invention can be preferably used as an active ingredient of pharmaceuticals.

EXAMPLES

The present invention will be explained more specifically with reference to the following examples. However, the scope of the present invention is not limited to these examples.

Example 1

4-[(5,6,7,8-Tetrahydro-5,5,8,8-tetramethyl-2-naphthalenyl)carbamoyl]benzoic acid (10.0 g) was added to a mixture of ethanol (130 mL) and water (120 mL) and dissolved with heating, and then the solution was gradually cooled and the precipitated crystals were collected by filtration. The resulting wet crystals were dried at 110° C. to 120° C. under reduced pressure to obtain crystals. The resulting crystals were subjected to differential scanning calorimetry, and as a result, the crystals gave a single endothermic peak approximately at 233° C. Further, the powder X-ray diffraction pattern of the crystals was identical to the powder X-ray diffraction pattern shown in FIG. 6 of Japanese Patent No. 3001632, which verified that the crystals were type-II crystals.

Example 2

Crystals were obtained in the same manner as in Example 1 except that the recrystallization solvent was changed to a mixture of ethanol (150 mL) and water (100 mL). The resulting crystals were subjected to differential scanning calorimetry, and as a result, the crystals gave a single endothermic peak approximately at 233° C. Further, the powder X-ray diffraction pattern of these crystals was identical to the powder X-ray diffraction pattern shown in FIG. 6 in Japanese Patent No. 3001632, which verified that the crystals were type-II crystals.

Example 3

Crystals were obtained in the same manner as in Example 1 except that the recrystallization solvent was changed to a mixture of ethanol (170 mL) and water (80 mL). The resulting crystals were subjected to differential scanning calorimetry, and as a result, the crystals gave two endothermic peaks approximately at 193° C. and 233° C. These crystals were termed as "type-III crystals".

Example 4

The type-III crystals obtained in Example 3 were heated at 200° C. to 205° C. for 2 hours under reduced pressure. The resulting crystals were subjected to differential scanning calorimetry, and as a result, the crystals gave a single endothermic peak approximately at 233° C. Further, the powder X-ray diffraction pattern of the resulting crystals was identical to the powder X-ray diffraction pattern shown in FIG. 6 in Japanese Patent No. 3001632, which verified that the crystals were type-II crystals.

Comparative Example 1

4-[(5,6,7,8-Tetrahydro-5,5,8,8-tetramethyl-2-naphthalenyl)carbamoyl]benzoic acid (20.0 g) was added to a mixture of methanol (200 mL) and water (20 mL) and dissolved with heating, and then cooled to room temperature. The solution was added dropwise slowly with water (40 mL), and the precipitated crystals were collected by filtration and dried at 110° C. to 120° C. under reduced pressure to obtain crystals. The resulting crystals were subjected to differential scanning calorimetry, and as a result, the crystals gave a single endothermic peak at approximately 193° C. Further, the powder X-ray diffraction pattern of these crystals was identical to the powder X-ray diffraction pattern shown in FIG. 5 of Japanese Patent No. 3001632, which verified that the resulting crystals were type-I crystals.

Test Example 1

Grain size distributions of the crystals obtained in Example 1 and Comparative Example 1 were measured. A laser-type grain size analyzer (Microtrac FRA) was used. A 1% aqueous solution of Soprophor FL (3 ml, Rhone-Poulenc) was added with water (15 ml), and an appropriate amount of the crystals obtained in Example 1 or Comparative Example 1 were dispersed in the mixture to obtain a sample dispersion. The results are shown in Table 1. As a result, the crystals obtained by the method of the present invention were revealed to have a smaller fluctuation in the average grain size, and found to be suitable for manufacture of tablets with uniform quality.

TABLE 1

| Average grain size | Methanol/water | Ethanol/water |
|---|---|---|
| 10% (μm) | 42.74 | 16.38 |
| 50% (μm) | 96.29 | 39.74 |
| 90% (μm) | 268.75 | 86.92 |

INDUSTRIAL APPLICABILITY

According to the method of the present invention, the type-II crystals stable against physical impact can be selectively prepared, and the crystals obtained are free from highly toxic hexane as a residual solvent. Accordingly, these crystals can be suitably used as active ingredients of pharmaceutical products. Further, the crystals obtained by the method of the present invention are characterized to have small fluctuation in average grain size, and enable preparation of tablets with a uniform content by a compression process.

What is claimed is:

1. A method of preparing a crystal of 4-[(5,6,7,8-tetrahydro-5,5,8,8-tetramethyl-2-naphthalenyl)-carbamoyl]benzoic acid, wherein the method comprises recrystallizing a starting crystal of 4-[(5,6,7,8-tetrahydro-5,5,8,8-tetramethyl-2-naphthalenyl)-carbamoyl]benzoic acid from a mixture of water and ethanol and affords a crystal of 4-[(5,6,7,8-tetrahydro-5,5,8,8-tetramethyl-2-naphthalenyl)-carbamoyl]benzoic acid which has a single endothermic peak approximately at 233° C. in differential scanning calorimetry and is suitable for use in a medicament.

2. The method of claim 1, wherein a volume ratio of ethanol and water is in a range of from about 8:5 to 1:1.

3. The method of claim 1, wherein a seed crystal is used in the recrystallization.

4. The method of claim 3, wherein a ratio of seed crystals to starting crystals is from about 1/1000 to 1/1,000,000.

5. The method of claim 4, wherein the ratio is about 1/80,000.

6. The method of claim 1, wherein the method further comprises drying the crystal at 110° C. to 120° C. under reduced pressure.

7. The method of claim 1, wherein after drying for 22 hours at 110° C. to 120° C. under a reduced pressure of 30 mmHg or lower the crystal of 4-[(5,6,7,8-tetrahydro-5,5,8,8-tetramethyl-2-naphthalenyl)-carbamoyl]benzoic acid contains not more than 2,000 ppm of residual ethanol.

8. The method of claim 7, wherein the crystal contains not more than 1,000 ppm of residual ethanol after drying.

9. The method of claim 7, wherein the crystal contains not more than 500 ppm of residual ethanol after drying.

10. A method of preparing a crystal of 4-[(5,6,7,8-tetrahydro-5,5,8,8-tetramethyl-2-naphthalenyl)-carbamoyl]benzoic acid, wherein the method comprises heating at a temperature of at least 180° C. a starting crystal of 4-[(5,6,7,8-tetrahydro-5,5,8,8-tetramethyl-2-naphthalenyl)-carbamoyl]benzoic acid having endothermic peaks approximately at 193° C. and 233° C. in differential scanning calorimetry and affords a crystal of 4-[(5,6,7,8-tetrahydro-5,5,8,8-tetramethyl-2-naphthalenyl)carbamoyl]benzoic acid which has a single endothermic peak approximately at 233° C. in differential scanning calorimetry and is suitable for use in a medicament.

11. A method of preparing a crystal of 4-[(5,6,7,8-tetrahydro-5,5,8,8-tetramethyl-2-naphthalenyl)-carbamoyl]benzoic acid, wherein the method comprises heating at a temperature of at least 200° C. a starting crystal of 4-[(5,6,7,8-tetrahydro-5,5,8,8-tetramethyl-2-naphthalenyl)-carbamoyl]benzoic acid having endothermic peaks approximately at 193° C. and 233° C. in differential scanning calorimetry and affords a crystal of 4-[(5,6,7,8-tetrahydro-5,5,8,8-tetramethyl-2-naphthalenyl)carbamoyl]benzoic acid which has a single endothermic peak approximately at 233° C. in differential scanning calorimetry and is suitable for use in a medicament.

12. A crystal of 4-[(5,6,7,8-tetrahydro-5,5,8,8-tetramethyl-2-naphthalenyl)-carbamoyl]benzoic acid, wherein the crystal has a single endothermic peak approximately at 233° C. in differential scanning calorimetry, does not contain hexane and/or ethyl acetate as a residual solvent and is suitable for use in a medicament.

13. A crystal of 4-[(5,6,7,8-tetrahydro-5,5,8,8-tetramethyl-2-naphthalenyl)-carbamoyl]benzoic acid, wherein the crystal has a single endothermic peak approximately at 233° C. in differential scanning calorimetry, contains not more than 2,000 ppm of residual ethanol when dried at 110° C. to 120° C. under reduced pressure, does not contain hexane and/or ethyl acetate as a residual solvent, and is suitable for use in a medicament.

14. A medicament comprising the crystal of claim 12.

15. A medicament comprising the crystal of claim 13.

* * * * *